BEST AVAILABLE COPY

United States Patent [19]

Hosoya et al.

[11] Patent Number: 5,023,175
[45] Date of Patent: Jun. 11, 1991

[54] NOVEL PRODUCTION PROCESS OF HYALURONIC ACID AND BACTERIUM STRAIN THEREFOR

[75] Inventors: Hideo Hosoya; Masayuki Kimura; Hiroshi Endo; Yoshio Hiraki; Shoji Yamamoto; Satoshi Yoshikawa; Hidetaka Omine; Koji Miyazaki, all of Tokyo, Japan

[73] Assignee: Kabushiki Kaisha Yakult Honsha, Tokyo, Japan

[21] Appl. No.: 38,907

[22] Filed: Apr. 16, 1987

[30] Foreign Application Priority Data

| May 1, 1986 [JP] | Japan | 61-99446 |
| May 1, 1986 [JP] | Japan | 61-99477 |
| Dec. 19, 1986 [JP] | Japan | 61-302922 |
| Mar. 19, 1987 [JP] | Japan | 62-64994 |

[51] Int. Cl.$^5$ .................... C12P 19/04; C12N 15/00; C12N 1/20
[52] U.S. Cl. .................. 435/101; 435/172.1; 435/253.4; 435/885
[58] Field of Search .............. 435/101, 172.1, 885, 435/253.4; 531/55.1, 55.2, 123, 55.3

[56] References Cited

U.S. PATENT DOCUMENTS 4,801,539 1/1989 Akasaka et al. .................. 435/101

FOREIGN PATENT DOCUMENTS 0144019 12/1985 European Pat. Off. .
2478468 9/1981 France .
2564859 11/1985 France .
8604355 7/1986 World Int. Prop. O. .

OTHER PUBLICATIONS

Bergey's Manual of Systematic Bacteriology, vol. 2, Williams & Wilkins, 1986.
Woolcock, J. B., J. of Gen. Microbiol. 85, pp. 372–375, 1974.
Chemical Abstract, vol. 82, No. 19, p. 247, May 12, 1975, Abstract No. 121419v, "Capsule of Streptococcus equi".

Primary Examiner—Douglas W. Robinson
Assistant Examiner—Irene Marx
Attorney, Agent, or Firm—Oblon, Spivak, McClelland, Maier & Neustadt, P.C.

[57] ABSTRACT

Hyaluronic acid can be produced efficiently and economically by culturing a strain belonging to a Streptococcus, which has hyaluronic acid producing ability, is hyaluronidase-nonproductive and shows anhemolytic property, and then collecting the hyaluronic acid from the resultant culture. The strain may preferably be Streptococcus zooepidemicus, especially, Streptococcus zooepidemicus YIT 2030 (FERM BP-1305). The hyaluronic acid has a high molecular weight and is useful in providing a cosmetic composition having excellent moisturizing effects and superb feeling of application.

2 Claims, 8 Drawing Sheets

NOVEL PRODUCTION PROCESS OF HYALURONIC ACID AND BACTERIUM STRAIN THEREFOR

BACKGROUND OF THE INVENTION

1. Field of the Invention:

This invention relates to a novel process for the production of hyaluronic acid and a bacterium strain useful in the process as well as a cosmetic composition containing hyaluronic acid of a high molecular weight and having high moisture-retaining effect and excellent feeling of application.

2. Description of the Prior Art:

It is now known that hyaluronic acid exists in every connective tissue in animal bodies. It is industrially obtained by extraction from living tissues such as fowl crests and umbilici. As its functions, hyaluronic acid has been reported to retain water among cells, to form gel-like matrices within cells to support the cells, to control intercellular movement of substances, and to protect cells from external physical shocks or infection with external bacteria, etc. Making effective use of these functions, hyaluronic acid is employed in pharmaceutical products (arthritic remedies, ophthalmic remedies, vulneraries, etc.), cosmetic compositions and so on.

The production of hyaluronic acid from living tissues by extraction is however unsuited for mass production and is costly, since the isolation and purification of hyaluronic acid is complex. This lies as a serious obstacle for the development of utility of hyaluronic acid.

As hyaluronic acid producing bacteria, there have already been known the bacteria of Group A, C and D under the Lancefield classification out of the bacteria of the *Streptococcus*, for example, *Streptococcus pyogenes*, *Streptococcus zooepidemicus*, *Streptococcus equi*, *Streptococcus equisimilis*, *Streptococcus dysgalactiae*, *Streptococcus faecalis var. zymoqenes*, *Pasteurella multocida*, etc. Production of hyaluronic acid has already been reported, for example, by Kendall et al. [F. E. Kendall et al., J. Biol. Chem., 118, 61 (1937)], Pierce et al. [W. A. Pierce et al., J. Bact., 63, 301 (1952)], MacLennan [A. P. MacLennan, J. Gen. Microbiol., 14, 134–142 (1956); J. Gen. Microbiol., 15, 485–491 (1956)], Holmström et al. [B. Holmström et al., Appln. 15, 1409–1413 (1967)], Woolcock [J. B. Woolcock, J. Gen. Microbiol., 85, 372–375 (1974)], Kjems et al. [E. Kjems et al., Acta Path. Microbiol. Scand. Sect. B, 84, 162–164 (1976)], Bergan et al. [T. Bergan et al., Acta Path. Microbiol. Scan., 75, 97–103 (1969)] and Cifonelli [J. A. Cifonelli, Carbohyd. Res., 14, 272–276 (1970)]. Mass production of hyaluronic acid was however not the objective in these reports. The culture was conducted using, as a carbon source, glucose at a concentration of 1–1.5%. The yields of hyaluronic acid were below 0.5–0.6 g/l, namely, below 6% based on the glucose. MacLennan states, in the above report, about the possibility of accelerated production of hyaluronic acid by culturing aerobically one of the bacteria of Group C under the Lancefield classification out of the bacteria of the *Streptococcus*. Among the above-described hyaluronic acid producing bacteria, the bacteria of Group A under the Lancefield classification out of the bacteria of the *Streptococcus* and the bacteria of the *Pasteurella* are known as pathogenic bacteria against human being and as a matter of fact, are unsuitable for mass culture.

Japanese Patent Laid-Open No. 56692/1983 discloses an industrial process in which a hyaluronic acid producing bacterium of the *Streptococcus* is cultured and hyaluronic acid is extracted from the resultant culture broth and is then purified. According to this process, one of the bacteria of Group A or C under the the Lancefield classification out of the bacteria of the *Streptococcus* was cultured to obtain hyaluronic acid in a large volume. Glucose was added as a carbon source at a concentration of 8% to a culture medium, followed by culture to obtain hyaluronic acid in a yield of 4 g/l. In this case, the yield of hyaluronic acid was 5% based on the glucose. This yield did not change when the concentration of added glucose was changed within a range of from 1% to 8%. Therefore, the yield of the hyaluronic acid based on the glucose is not substantially different from that achieved by the hyaluronic acid producing bacteria in the above-described reports. As other processes for obtaining hyaluronic acids by using bacteria of the *Streptococcus*, reference may be had to Japanese Patent Laid-Open Nos. 500597/1985, 133894/1985 and 15698/1986. These processes are however accompanied by one or more problems such that the resulting hyaluronic acid has a low molecular weight or its yield is low. Such hyaluronic acid producing bacterium strains are also known to produce a streptolysin (soluble hemolysin) and exhibit $\beta$ hemolysis. If one tries to produce hyaluronic acid by culturing such a bacterium on a large scale, there is a potential danger that the hemolysin could mix in the product, i.e., hyaluronic acid. It is not preferable to add such hyaluronic acid in cosmetic or pharmaceutical products.

In order to improve the above-described drawback, Japanese Patent Laid-Open No. 251898/1985 discloses to obtain hyaluronic acid by culturing a hyaluronic acid producing bacterium strain the streptolysin producing capacity of which has been eliminated by a mutation with a mutagen. This patent publication also describes that hyaluronic acid was obtained in a yield of 3.6 g/l by adding 6% of glucose. Here, the yield of hyaluronic acid is 6% based on the glucose. The productivity is still low in view of the yield of hyaluronic acid based on the glucose.

By the way, moisturizing (water-retaining) agents such as polyols, skin components and biopolymers are added in cosmetic compositions in order to protect the skin from external irritation and skin chapping and to improve the feeling of application when the cosmetic compositions are applied to the skin. Among such skin components, hyaluronic acid is said to take part in the retention of water in the human skin. It is recently added to cosmetic compositions and exhibits excellent moisturizing effects [Fragrance Journal, 79, 64–71 (1986)]. The molecular weight of hyaluronic acid, which has conventionally been added to cosmetic compositions, is however as low as 300,000–1,500,000 and its moisturizing effects are still not fully satisfactory.

SUMMARY OF THE INVENTION

Accordingly, an object of this invention is to provide an economical and efficient process suitable for the mass production of hyaluronic acid by using a bacterium strain.

Another object of this invention is to provide a bacterium strain for use in the practice of the above process.

A further object of this invention is to provide a cosmetic composition containing hyaluronic acid and having excellent moisturizing effects and superb feeling of application.

With the foregoing in view, the present inventors have carried out a variety of investigation on the production of hyaluronic acid. As a result, it has been found that a bacterium strain obtained by subjecting to a further mutation treatment a bacterium strain, which has been obtained by mutating a hyaluronic acid producing bacterium of the *Streptococcus zooepidemicus* isolated from the nature and does not exhibit hemolysis, does not have any hyaluronidase producing ability any longer but has extremely high hyaluronic acid producing ability; hyaluronic acid produced using the former bacterium strain has a greater molecular weight, i.e., 2,000,000 or higher compared with conventional hyaluronic acid and has excellent moisturizing effects; and the addition of the thus-obtained hyaluronic acid can provide cosmetic compositions having excellent moisturizing effects and superb feeling of application.

In one aspect of this invention, there is thus provided a process for the production of hyaluronic acid, which comprises the following steps:

culturing in a culture medium a strain belonging to a *Streptococcus* which has hyaluronic acid producing ability, is hyaluronidase-nonproductive and shows anhemolytic property; and collecting the hyaluronic acid from the resultant culture.

In another aspect of this invention, there is also provided a *Streptococcus zooepidemicus* which has hyaluronic acid producing ability, is hyaluronidase-nonproductive and shows anhemolytic property.

In a further aspect of this invention, there is also provided a cosmetic composition comprising hyaluronic acid having a molecular weight of at least 2,000,000 or a salt thereof.

The mutant of *Streptococcus zooepidemicus* of this invention can provide hyaluronic acid, which is absolutely free of mingled streptolysins and has a high molecular weight, in a high yield and with high productivity, far better than its yields and productivities in the conventionally-reported process for the production of hyaluronic acid by bacteria of the *Streptococcus*, and moreover at a low cost. The thus-produced hyaluronic acid is ideal as a raw material for cosmetic and pharmaceutical products. When added to cosmetic compositions in particular, hyaluronic acid of this invention the molecular weight of which is 2,000,000 or higher shows extremely superior moisturizing effects to hyaluronic acid having a molecular weight of 1,500,000 or lower and added conventionally in cosmetic compositions. Accordingly, the cosmetic composition of this invention, which is added with the former hyaluronic acid, has high moisturizing effects and is extremely good in feeling of application, for example, its spreadability along the skin, the moisturized feeling of the skin, and the smoothness (softness) to the skin, etc.

BRIEF DESCRIPTION OF THE DRAWINGS

The above and other objects, features and advantages of the present invention will become apparent from the following description and the appended claims, taken in conjunction with the accompanying drawings, in which:

FIG. 1 is a diagram showing the progress of culture of the hyaluronic acid producing bacterium in Example 2 of the present invention;

FIG. 2 is a diagram showing the progress of the culture in Example 3;

FIG. 3 is an IR absorption spectrum of high molecular hyaluronic acid obtained in Example 2;

FIG. 4 is an NMR spectrum of the high molecular hyaluronic acid;

FIGS. 5 through 7 diagrammatically illustrate variations in skin-surface water content as a function of time elapsed after separate application of the toilet waters of Example 4;

FIG. 8 diagrammatically illustrates variations in skin-surface water content as a function of time elapsed after separate application of the toilet waters of Example 5; and FIGS. 9 and 10 diagrammatically illustrate average values of the skin-surface water content up to 60 minutes after separate application of the toilet waters of Example 6.

DETAILED DESCRIPTION OF THE INVENTION AND PREFERRED EMBODIMENTS

The *Streptococcus zooepidemicus* of this invention which has hyaluronic acid producing ability, is hyaluronidase-nonproductive and shows anhemolytic property can be obtained, for example, in the following manner. First of all, a *Streptococcus zooepidemicus* which has strong hyaluronidase producing ability and belongs to Group C under the Lancefield classification is obtained from the nasal mucous membrane [the identification of the bacterium was conducted following Bergey's Manual of Determinative Bacteriology, 8th edition (1974)]. As indicated by MacLennan [MacLennan, J. Gen. Microbiol., 14, 134–142 (1956)], the above bacterium strain produced hyaluronic acid very well under aerobic conditions and when glucose was used as a carbon source, yielded 2 g/l of hyaluronic acid upon addition of 4% of glucose (yield of hyaluronic acid: 5% based on the glucose). The molecular weight of the thus-obtained hyaluronic acid was 300,000–600,000. Following the routine practice [Bacteria/Phage Genetic Laboratory Techniques, Special Edition of "Proteins-Nucleic Acids-Enzymes", The Kyoritsu Publishing Co., Ltd. (1972)], the bacterium strain was treated with ultraviolet rays or a mutagen [N-methyl-N'-nitro-N-nitrosoguanidine (NTG), ethyl methanesulfonate, or the like]. The thus-treated cells were mixed and inoculated in a blood agar culture medium. A bacterial colony showing no hemolysis was collected. After subjecting the resultant bacterium strain again to the mutation, it was coated on a nutrient agar culture medium which contained hyaluronic acid. A bacterial colony in which hyaluronic acid was not decomposed was collected to obtain a mutant of *Streptococcus zooepidemicus* (see Example 1 which will be described subsequently).

The thus-obtained mutant of *Streptococcus zooepidemicus* (hereinafter called "the present bacterium") formed a transparent bacterial colony, which had extremely strong viscosity, on a Todd-Hewitt broth agar culture medium. It is a bacterium of the *Streptococcus* which is anhemolytic (β hemolysis: negative), is hyaluronidase-nonproductive and belongs to Group C under the Lancefield classification. The present bacterium has the following mycological characteristics:

| | |
|---|---|
| (a) Gram stain: | Positive. |
| (b) 10° C. Growth: | Negative. |
| (c) 45° C. Growth: | Negative. |
| (d) 0.1% Methylene blue resistance: | Negative. |

| | | |
|---|---|---|
| (e) 6.5% Saline resistance: | Negative. |
| (f) 40% Bile resistance: | Negative. |
| (g) Bacitracin resistance: | Positive. |
| (h) pH 9.6 Resistance: | Negative. |
| (i) 60° C.-30 Minutes resistance: | Negative. |
| (j) Gelatin liquefying capacity: | Negative. |
| (k) Starch decomposing capacity: | Positive. |
| (l) Sodium hippurate decomposing capacity: | Negative. |
| (m) Esculin decomposing capacity: | Weak positive. |
| (n) Arginine decomposing capacity: | Positive. |
| (o) Glycofermentativeness: Glucose, galactose, sucrose, lactose, maltose, sorbitol and salicin: | Positive. |
| Glycerin, mannitol, trehalose and arabinose: | Negative. |

From the above-described mycological characteristics of the present bacterium, the present bacterium "Streptococcus zooepidemicus YIT 2030" and deposited it under FERM BP-1305 with the Fermentation Research Institute, Agency of Industrial Science and Technology, Ministry of International Trade and Industry, the Japanese Government.

A description will next be made of a process for culturing the present bacterium and then collecting hyaluronic acid having a molecular weight of 2,000,000 or higher from the resultant culture broth.

The culture medium, which is employed to culture the present bacterium to obtain hyaluronic acid, may preferably contain a carbon source, organic and inorganic nitrogen sources, and if necessary, inorganic salts and organic micronutrients. As a carbon source, it is preferable to use a carbon source which contains sugar or its analogous substance, such as glucose, galactose, sucrose, lactose, fructose, maltose, sorbitol or a starch hydrolyzate. As an alternative, an organic acid, aliphatic alcohol or the like may also be used. As nitrogen sources, usual material can be used for both organic and inorganic nitrogen sources. Various meat extracts, amino acid mixtures, peptone, yeast extract, etc. are however preferred. In addition, there may be added one or more of the chlorides, sulfates, phosphates, nitrates and carbonates of sodium, potassium, calcium, magnesium, iron and the like and vitamins as needed.

Aerobic conditions are essential for the culture. It is recommended to increase the stirring speed as the viscosity of the culture broth increases. However, excessive stirring is not preferred. The culture temperature may preferably be 25-38° C. in which the present bacterium is allowed to grow. Since the present bacterium produces lactic acid during its culture and the growth of the present bacterium and the production of hyaluronic acid are both suppressed by the lactic acid, it is also preferable to add an aqueous solution of an alkali for the neutralization of lactic acid so that the pH of the culture broth is maintained within a range of 6-8. As an aqueous alkali solution useful for the above purpose, may be mentioned an aqueous solution of sodium hydroxide or potassium hydroxide or aqueous ammonia.

The present bacterium produces hyaluronic acid of a high molecular weight (molecular weight: 2,000,000 or higher) in an extremely high yield and productivity. Particularly good results are obtained when glucose is used as a carbon source. Namely, an addition of glucose can improve the productivity of the intended product, i.e., hyaluronic acid to a significant extent. Glucose may be added preferably in an amount of 0.5-6%.

The present bacterium does not permit accumulation of any high molecular substances other than hyaluronic acid in the culture broth. It is therefore easy to isolate and purify hyaluronic acid, which has accumulated in the culture broth, after the culture. This can be done by one of conventionally-known isolation and purification methods for polysaccharides.

An isolation and purification method of hyaluronic acid will next be described by way of example. A culture broth is diluted with water so as to reduce its viscosity to a suitable level (preferably to 100 cps or lower), followed by adjustment of its pH to 4 or lower with trichloroacetic acid. Thereafter, cells are separated and removed by centrifugation or membrane filtration (pore size: 0.2 μm or smaller). After removal of low molecular substances dissolved in the solution by ultrafiltration, dialysis, organic solvent precipitation or adsorption on an ion-exchange resin, hyaluronic acid having a molecular weight of 2,000,000 or higher can be obtained by a method such as organic solvent precipitation, freeze drying or spray drying.

Comparing with a standard sample of hyaluronic acid (molecular weight: about 630,000; product of Sigma Chemical Company), a variety of study was conducted on the hyaluronic acid which was obtained by extracting it from the above-described culture broth and then purifying same. As a result, the product was confirmed to be hyaluronic acid. Its properties will next be described.

(1) It showed the same mobility as the sample in an electrophoretic experiment in which a cellulose acetate membrane was used.

(2) It was decomposed by a Actinomycetes hyaluronidase (product of Amano Pharmaceutical Co., Ltd.). When the decomposition product was subjected to thin-layer chromatography on a silica gel plate, two spots appeared at the same mobilities as those showed up upon TLC of a decomposition product of the sample treated int eh same manner.

(3) When the chemical composition of the decomposition product was analyzed, N-acetyl-D-decomposition product was analyzed, N-acetyl-D-glucosamine and D-glucuronic acid were found to exist at a molar ratio of 1:1.

(4) Specific rotatory power $[\alpha]^{20}_D = -69°$.

(5) An infrared absorption spectrum of the hyaluronic acid by the thin film method is shown in FIG. 3 and is hence identical to an infrared absorption spectrum of the sample.

(6) A $^{13}$C-NMR spectrum measured by dissolving the hyaluronic acid in heavy water is depicted in FIG. 4 and is hence identical to a $^{13}$C-NMR spectrum of the sample.

(7) The molecular weight of the hyaluronic acid was found to range from 2,000,000 to 3,000,000 as a result of its measurement by the viscosity measurement method [T. C. Laurent et al., Biochim. Biophys. Acta, 42, 476-485 (1960)].

To a cosmetic composition of this invention, the above-described hyaluronic acid having a molecular weight of 2,000,000 or higher, or its salt may preferably be added in an amount of 0.005-3.0 wt% (hereinafter referred to merely as "%"), especially, 0.05-2.0%. As exemplary salts of hyaluronic acid, may be mentioned the sodium salt, potassium salt, lithium salt, magnesium salt, calcium salt, lysine salt, ammonium salt, triethanolamine salt, propanolamine salt, etc.

The cosmetic composition of this inveniton can be formulated into desired forms, for example, various creams, milky lotions, toilet waters, essences, packs, hair rinses, hear treatments, shampoos, lip sticks, foundations, hair growth stimulants, etc. by suitably adding the above-described hyaluronic acid in combination with various oils, surfactants, antiseptics, viscosity modifiers and pharmaceutically effective agents, perfumes, alcohols, water, etc., which are usually incorporated in cosmetic compositions, and other wetting agents if necessary.

The following more specific substances may be mentioned as illustrative examples of the aforementioned additional ingredients: as oils, mineral oil, petrolatum, paraffin wax, squalane, bees wax, higher alcohols, fatty acids, etc.; as surfactants, polyoxyethylene fatty acid esters, polyoxyethylene sorbitan fatty acid esters, glycerin fatty acid esters, polyoxyethylene glycerin fatty acid esters, polyoxyethylene-hydrogenated castor oil, polyoxyethylene sorbitol fatty acid esters, etc.; as alcohols, ethanol, etc.; as viscosity modifiers, carboxymethylcellulose, hydroxyethylcellulose, polyvinyl alcohol, carboxy vinyl polymer, xanthan gum, etc.; as wetting agents, sorbitol, glycerin, culture broths of lactic acid bacteria, 1,3-butylene glycol, sodium pyrrolidonecarboxylate, sodium lactate, polyethylene glycol, etc.; as antiseptics, alkyl para-hydroxybenzoates, sodium benzoate, potassium sorbitate, etc.; as pharmaceutically effective agents, vitamins, antiphlogistics, disinfectants, etc.

A cosmetic composition added with a culture broth of a lactic acid bacterium out of the above-described optional ingredients enjoys especially good moisturizing effects and feeling of application.

A culture broth of a lactic acid bacterium, useful in the present invention, may be produced in a usual manner, namely, by inoculating the lactic acid bacterium on a culture medium composed principally of a beast milk such as cow milk, conducting lactic acid fermentation and then collecting milk serum from the resultant culture broth.

As the lactic acid bacterium, may be employed *Lactobacillus acidophilus, Lactobacillus bulgaricus, Lactobacillus casei* or *Streptococcus thermophilus* by way of example. The beast milk employed as a culture medium may be any one of human milk, cow milk, goat milk and the like. It may also be skim milk of such a beast milk or a milk reconstituted from a powdered milk (including a powdered skim milk). Of these, a skim milk or reconstituted skim milk is particularly preferred, because it facilitates treatments after lactic acid fermentation. To the culture medium, it is desirable to add glucose or sucrose, which is effective for the promotion of growth of the lactic acid bacterium, in addition to the beast milk. It is unnecessary to use any special culture conditions. As standard conditions, a culture medium such as that mentioned above is heated and sterilized at 115° C. for 15 minutes or so (or at 110° C. for 90 minutes), followed by inoculation of the lactic acid bacterium. The lactic acid bacterium is then cultured at 37° C. for 2-3 days.

Milk serum is then collected from the resultant culture broth by filtration or centrifugal separation.

The thus-obtained milk serum, namely, the culture broth of the lactic acid bacterium may be used as is. However, the milk serum has certain specific smell. It is therefore preferable, in the present invention, to heat the milk serum under reduced pressure prior to the use of the milk serum as in Japanese Patent Laid-Open No. 192811/1983 so that a portion of the milk serum is distilled off until fragrant components of the milk serum are removed substantially. The culture broth of the lactic acid bacterium may also be used in a concentrated form.

The culture broth of the lactic acid bacterium may preferably be added in an amount of 0.1-90%, although its amount varies the degree of its concentration and the form of the cosmetic composition.

The moisturizing effects can be improved further if 1,3-butylene glycol is incorporated in addition to the high molecular hyaluronic acid of this invention and the culture broth of the lactic acid bacterium. 1,3-Butylene glycol may preferably be added in an amount of 0.05-20% with 1-10% being particularly preferred.

Having generally described the invention, a more complete understanding can be obtained by reference to certain specific examples, which are provided herein for purposes of illustration only and are not intended to be limiting unless otherwise specified.

EXAMPLES

The present invention will hereinafter be described in detail by the following Examples.

EXAMPLE 1:

A *Streptococcus zooepidemicus*, which had been collected from the nasal mucous membrane of a bovine and exhibited ( hemolysis and produced both hyaluronidase and hyaluronic acid, was cultured at 37° C. for 10 hours in a Todd-Hewitt agar culture medium (product of Difco Company). Cells in their logarithmic growth phase were collected by centrifugation. While repeating their centrifugation at a low temperature, they were washed twice with a 0.05-M tris-maleic acid buffer (pH 6.0) under sterile conditions. The thus-washed cells were then dispersed in a fresh supply of the same buffer to a concentration of $1 \times 10^8$ cells/ml, to which NTG was added to a concentration of 200 $\mu$g/ml. The resulting mixture was shaken at 37° C. for 30 minutes. After washing the cells twice with a 0.05-M tris-maleic acid buffer (pH 6.0) at a low temperature, they were inoculated in a Todd-Hewitt broth culture medium and cultured at 37° C. for 18 hours. The resulting culture broth was then diluted with a sterilized physiological saline to reduce the concentration of the cells to $1 \times 10^3$ cells/ml. After mixing and diluting 0.1 ml of the thus-diluted culture broth in a blood (defibrinated rabbit blood) agar culture medium (20 ml) and then culturing the cells, a bacterial colony showing no hemolysis was collected. The frequency of obtainment of the mutant was about $4 \times 10^{-6}$. In the same manner as in the above procedure, the anhemolytic bacterium strain was next cultured at 37° C. in a Todd-Hewitt broth culture medium and cells in their logarithmic growth phase were collected. After washing the cells with a 0.05-M trismaleic acid buffer (pH 6.0), they were shaken at 37° C. for 20 minutes in a fresh supply of the same buffer with 200 $\mu$g/ml of NTG added thereto. After washing the cells at a low temperature with a further fresh supply of the same buffer, they were inoculated in an ultrafiltrated culture medium (which was obtained by removing high molecular fractions from a Todd-Hewitt broth culture medium by means of an ultrafiltration membrane "YM-10" produced by Amicon Company) and were cultured at 37° C. for 18 hours. The resultant culture broth was diluted to a concentration of $1-5 \times 10^2$ cells/ml with a sterilized physiological saline. On an ultrafiltrated agar culture medium (high-purity agar) which was of the same type as that described above and contained 0.1% of sodium hyaluronate (molecular weight: about 630,000; product of Sigma Chemical Company), 0.1 ml of the above-diluted culture broth was coated. The cells were then cultured at 37° C. for 20-40 hours in a moisture chamber. Cells in a grown colony were collected by the replica plating technique. The agar was sprayed with a 10% aqueous solution of cetylpyridinium chloride. From about 500,000 cells, cells of a hyaluronidase-nonproductive mutant forming a colony with a clouded peripheral part, Streptococcus zooepidemicus YIT 2030, were obtained.

Incidentally, the identification of the abovementioned hyaluronidase-productive and nonproductive bacterium strains was conducted by modifying the method of Erika-Balke et al. [Erika-Balke et al., Zbl. Bakt. Hyg. A, 259, 194-200, (1985)].

EXAMPLE 2

Batchwise culture

Placed in a 10-l jar fermenter was a culture medium (pH 7.0) having the following composition: 6% of glucose, 1.5% of polypeptone (product of Daigo Eiyo Kagaku K.K.), 0.5% of a bakery yeast extract (product of Oriental Yeast Co., Ltd.), 0.2% of dipotassium hydrogenphosphate, 0.1% of magnesium sulfate heptahydrate, 0.005% of calcium chloride and 0.001% of "Adekanol LG-109" (trade mark; defoaming and antifoaming agent; product of Asahi Denka Kogyo K. K.). After sterilizing the culture medium, the culture medium was inoculated with 1% of Streptococcus zooepidemicus YIT 2030 which had been cultured in advance. While continuously controlling the pH of the culture broth at 7 with a 6-N aqueous solution of sodium hydroxide, the bacterium was cultured at 37° C. for 42 hours under aeration and stirring.

Glucose was sterilized separately and added at once at the initiation of the culture. The progress of the culture is illustrated in FIG. 1. As the culture proceeded, more and more hyaluronic acid was accumulated. In 29 hours of the culture, the viscosity of the culture broth increased close to 8,000 cps and the culture broth showed almost no fluidity. Upon an elapse time of 42 hours since the initiation of the culture, the culture was finished when the concentration of glucose had reached zero in the culture broth.

Since the thus-obtained culture broth had no fluidity, it was diluted with water to a viscosity of 100 cps or lower. Thereafter, the thus-diluted solution was adjusted to pH 4 with trichloroacetic acid and then caused to pass through a hollow-fiber microfilter module ("PW-103", trade name; manufactured by Asahi Chemical Industry Co., Ltd.) to remove cells and insoluble components. The filtrate was caused to pass through a hollow-fiber ultrafiltration membrane ("HIP 30-43", trade name; product of Amicon Company) while charging water to the internal solution, thereby removing low molecular substances from the filtrate. The thus-obtained solution was then dried by the freeze drying method to obtain 6.7 g of hyaluronic acid per liter of the culture broth. The molecular weight of the resultant hyaluronic acid was about 2,160,000 (as measured by the viscosity measurement method).

EXAMPLE 3

Continuous culture

Placed in a 10-l jar fermenter was 5 l of a culture medium of the same composition as that employed in Example 2 except that the concentration of glucose was changed to 2.5%. After sterilization (glucose was sterilized separately), pre-cultured Streptococcus zooepidemicus YIT 2030 was inoculated in an amount of While controlling the pH of the culture broth at 7 with a 6-N aqueous solution of sodium hydroxide, the bacterium was cultured at 37° C. for 15 hours under aeration and stirring. While continuously feeding at a dilution rate of 0.3 hr$^{-1}$ a culture medium of the same type as that employed in Example 2 except for the change of the glucose concentration to 2%, continuous culture was conducted at 37° C. and pH 7 for 1 week under aeration and stirring. The progress of the culture is illustrated in FIG. 2. The culture broth, which flowed out of the culture tank, was collected periodically and hyaluronic acid (molecular weight: about 2,160,000 as measured in accordance with the viscosity measurement method) was extracted and purified in the same manner as in Example 2. As a result, the yield of hyaluronic acid was 15% based on the glucose and its productivity was 0.9 g/l/hr. It was possible to obtain 21.6 g/l of hyaluronic acid per day.

EXAMPLE 4

A toilet water of a composition shown in Table 1 was prepared. Its moisturizing effects upon coated on the human skin were tested in accordance with the measurement method of skin-surface dielectric constant [Karl Mosler, Sonderdruck aus Parfümerie und Kosmetik, 64, 375-379 (1983)], which is an improvement to the electrical measurement method proposed by Tagami et al. [Tagami et al., J. Invest. Dermatol., 75, 500-507 (1980)]. In Table 1, hyaluronic acid prepared from rooster combs (product of Teikoku Hormone Mfg., Co., Ltd.) was used as the low molecular hyaluronic acid while the product of Example 2 was employed as the high molecular hyaluronic acid. Further, numeral values given in Table 1 are all by wt.%.

TABLE 1

| Component | Control C-1 | Invention product 1 | 2 | 3 | Comparative product 1 | 2 | 3 |
|---|---|---|---|---|---|---|---|
| High molecular sodium hyaluronate (m.w. 2,160,000) | — | 0.1 | 0.3 | 0.5 | — | — | — |
| Low molecular sodium hyaluronate (m.w. 780,000) | — | — | — | — | 0.1 | 0.3 | 0.5 |
| 1,3-Butylene glycol | 2 | 2 | 2 | 2 | 2 | 2 | 2 |
| Ethanol | 10 | 10 | 10 | 10 | 10 | 10 | 10 |
| Purified water | Balance to 100 | Balance to 100 | Balance to 100 | Balance to 100 | Balance to 100 | Balance to 100 | Balance to 100 |

Testing Method

After washing internal forearm skin of healthy male volunteers (27 years old) with soap, an area 4×4 cm was marked at three test sites on each of the left and right brachia of each of the volunteers, i.e., at 6 test sites in total. About 30 minutes later, the skin-surface dielectric constant before application of a toilet water was measured three times at each test sites with a skin-surface moisture analyzer ("SKICOS 3", trade name; manufactured by Amic Group K.K.; probe diameter: 16 mm) and an average value was then calculated. Immediately after that, 30 μl portions of a sample toilet water were applied to the respective test sites (16 cm$^2$) as uniformly as possible with fingers. After the application, the skin-surface dielectric constant at each test sites was measured periodically three times at each time and average values were calculated. Skin-surface water contents were then calculated respectively from the skin-surface dielectric constants in accordance with the above-mentioned literature [Karl Mosler, Sonderdruck aus Parfümerie und Kosmetik 64, 375–379 (1983)]. Expressing the skin-surface water content before the application of the sample in terms of 0, the skin-surface water contents were shown as variations. In order to minimize the differences among the test sites and other errors, the test sites to be applied with the toilet water were changed and the above measurement was repeated 6 times. Their average value was employed. During the above measurements, the room temperature was 27–29° C. while the relative humidity was 45–70%.

Test Results

Results are shown in FIG. 5–FIG. 7, which show higher moisturizing effects as the skin-surface water content increases. As a result, the toilet waters of this invention which contained the high molecular hyaluronic acid had superior moisturizing effects to the comparative products containing the low molecular hyaluronic acid.

EXAMPLE 5

Toilet waters of compositions given in Table 2 were prepared and applied on the human skin. Their moisturizing effects were tested by measuring skin-surface water contents. Skin-surface water contents were determined from skin-surface dielectric constants measured in the same manner as in Example 4. Expressing the skin-surface water content before the application of the sample in terms of 0, the skin-surface water contents were shown in terms of increments in skin-surface water content. Results are depicted in FIG. 8. Incidentally, the relative humidity and room temperature at the time of the measurement were 44±2% and 26±1° C. respectively. In Table 2, hyaluronic acid having a molecular weight of about 780,000 (product of Teikoku Hormone Mfg., Co., Ltd.) was used as the low molecular hyaluronic acid while the product of Example 2 was employed as the high molecular hyaluronic acid. Further, numeral values given in Table 1 are all by wt.%.

TABLE 2

| Ingredient | Control C-2 | Control C-3 | Invention Product 4 | Invention Product 5 | Invention Product 6 | Comp. Product 4 |
|---|---|---|---|---|---|---|
| High molecular sodium hyaluronate (molecular weight: 2,160,000) | — | — | 0.05 | 0.1 | 0.2 | — |
| Low molecular sodium hyaluronate (molecular weight: 780,000) | — | — | — | — | — | 0.2 |
| 1,3-Butylene glycol | — | 2 | 2 | 2 | 2 | 2 |
| Ethanol | — | 8 | 8 | 8 | 8 | 8 |
| Methyl para-hydroxybenzoate | — | 0.12 | 0.12 | 0.12 | 0.12 | 0.12 |
| Purified water | Balance to 100 | Balance to 100 | Balance to 100 | Balance to 100 | Balance to 100 | Balance to 100 |
| pH | 6.2 | 6.2 | 6.2 | 6.2 | 6.2 | 6.2 |

As a result, all of the toilet waters of this invention showed excellent moisturizing effects compared with the toilet water which contained the low molecular hyaluronic acid.

EXAMPLE 6

Toilet waters of compositions shown in Table 3 were prepared. Skin-surface water contents were determined in the same manner as in Example 4. Results are shown in Table 4. The results, which were averaged values of the skin-surface water contents at the 10th, 20th, 30th, 45th and 60th minutes after application are shown in FIGS. 9 and 10 respectively. During the measurement, the relative humidity and room temperature were 27±7% and 26±2° C. respectively. In Tables 3 and 4, hyaluronic acid having a molecular weight of about 780,000 (product of Teikoku Hormone Mfg., Co., Ltd.) was used as the low molecular hyaluronic acid while the product of Example 2 was employed as the high molecular hyaluronic acid. As the culture broth of the lactic acid bacterium, milk serum was used [in an amount of 0.016 g (dry weight)/ml] after removal of fragrant components (the same milk serum was also used in the subsequent Examples).

TABLE 3

| Ingredient | Invention Product 7 | Invention Product 8 | Comparative Product 5 | Comparative Product 6 |
|---|---|---|---|---|
| Culture broth of lactic acid bacterium | 97.65 | 97.65 | 97.65 | 97.65 |
| Sodium hyaluronate (m.w. 2,160,000) | 0.2 | 0.2 | — | — |
| Sodium hyaluronate (m.w. 780,000) | — | — | 0.2 | 0.2 |
| 1,3-Butylene glycol | — | 2.0 | — | 2.0 |
| Methyl para-hydroxybenzoate | 0.15 | 0.15 | 0.15 | 0.15 |
| Purified water | 2.0 | — | 2.0 | — |
| (pH) | 6.0 | 6.0 | 6.0 | 6.0 |

TABLE 4

| Toilet water | Increment in skin-surface content after application (mgH$_2$O/cm$^2$) | | | | | Average value |
|---|---|---|---|---|---|---|
| | 10 min. later | 20 min. later | 30 min. later | 45 min. later | 60 min. later | |
| Invention Product 7 | 0.69 | 0.62 | 0.58 | 0.61 | 0.63 | 0.62 |
| Invention Product 8 | 1.30 | 1.11 | 1.05 | 0.92 | 1.02 | 1.08 |
| Comparative Product 5 | 0.40 | 0.40 | 0.31 | 0.29 | 0.37 | 0.35 |
| Comparative Product 6 | 0.97 | 0.78 | 0.78 | 0.75 | 0.76 | 0.81 |

From the above results, it is understood that the toilet waters containing high molecular hyaluronic acid had superior moisturizing effects to the toilet waters containing low molecular hyaluronic acid. The toilet water of this invention containing 1,3-butylene glycol additionally had still better moisturizing effects.

EXAMPLE 7

Toilet waters of the compositions given in Table 5 were prepared. The feeling of their application was evaluated. Numerical values in Table 5 are by wt.%.

TABLE 5

| Ingredient | Comparative Product 7 | Comparative Product 8 | Invention Product 9 | Invention Product 10 |
|---|---|---|---|---|
| High molecular sodium hyaluronate (molecular weight: 2,160,000) | — | — | 0.05 | 0.1 |
| Low molecular sodium hyaluronate (molecular weight: 780,000) | — | 0.2 | — | — |
| Ethanol | 8.0 | 8.0 | 8.0 | 8.0 |
| 1,3-Butylene glycol | 2.0 | 2.0 | 2.0 | 2.0 |
| Methyl para-hydroxybenzoate | 0.12 | 0.12 | 0.12 | 0.12 |
| Perfume | 0.15 | 0.15 | 0.15 | 0.15 |
| Purified water | Balance to 100 | Balance to 100 | Balance to 100 | Balance to 100 |

Evaluation Method and Results

Each of the toilet waters of Table 5 was applied in a predetermined amount to the backs of the hands of 10 panellers (5 male panellers and 5 female panellers). It was evaluated by having each paneller fill out a questionnaire with respect to its spreadability on the skin, frictional feeling, stickiness, high-quality feeling, smoothness and moisturizing effects.

As a result, Invention Product 10 was found to show significantly superior feeling of application to both Comparative Products 7 and 8. Invention Product 9 exhibited significantly superior feeling of application to Comparative Product 7 and comparable feeling of application to Comparative Product 8. Accordingly, high molecular hyaluronic acid, which is added in accordance with this invention, can show similar effects to conventional low molecular hyaluronic acid when the former is added in an amount one fourth the latter.

EXAMPLE 8

A milky lotion of the following composition was and the feeling of its application was evaluated.

| Composition: | |
|---|---|
| Stearic acid | 2.5 wt. % |
| Beef tallow | 1.5 |
| Mineral oil | 6.0 |
| Methyl para-hydroxybenzoate | 0.3 |
| Sorbitan monostearate | 1.5 |
| Polyoxyethylene sorbitan monooleate (20 E.O.) | 2.5 |
| 1,3-Butylene glycol | 6.0 |
| High molecular sodium hyaluronate (molecular weight: 2,160,000; obtained in Example 2) | 0.2 |
| Perfume | 0.2 |
| Purified water | Balance to 100 |

Evaluation Method and Results

Each of the above milky lotion of this invention and a toilet water of the same composition except for the addition of the sodium salt of low molecular hyaluronic acid (molecular weight: about 780,000; product of Teikoku Hormone Mfg., Co., Ltd.) in the same amount in place of the high molecular sodium hyaluronate was used for 3 days by 13 professional panellers. They were evaluated by having each paneller fill out a questionnaire with respect to four characteristics including spreadability on the skin, stickiness, high-quality feeling, smoothness and moisturizing effects.

As a result, the milky lotion of this inveniton was found to be superior to a milky lotion of the same composition except for the addition of the low molecular sodium hyaluronate, especially, in spreadability on the skin and moisturizing effect to the skin.

EXAMPLE 9

A cream of the following composition was prepared and the feeling of its application was evaluated.

| Composition: | |
|---|---|
| Mineral oil | 23.0 wt. % |
| Octyldodecyl myristate | 5.0 |
| Petrolatum | 6.0 |
| Bees wax | 5.0 |
| Stearic acid | 2.0 |
| Behenyl alcohol | 1.0 |
| Sorbitan monostearate | 3.0 |
| Polyoxyethylene sorbitan monostearate (20 E.O.) | 3.0 |
| 1,3-Butylene glycol | 3.0 |
| Methyl para-hydroxybenzoate | 0.3 |
| High molecular sodium hyaluronate (molecular weight: 2,160,000; obtained in Example 2) | 0.2 |
| Perfume | 0.2 |
| Purified water | Balance to 100 |

Evaluation Method and Results

As a result of an evaluation conducted in the same manner as in example 7, the cream of this inveniton did not have stickiness as opposed to a cream of the same composition except for the addition of the low molecular sodium hyaluronate and was superior to the latter cream, especially, in smoothness to the skin and moisturizing effects.

EXAMPLE 10

A toilet water of the following composition was prepared.

| Composition: | |
|---|---|
| Ethanol | 10.0 wt. % |
| 1,3-Butylene glycol | 2.0 |
| High molecular sodium hyaluronate (molecular weight: 2,160,000; obtained in Example 2) | 0.2 |
| Polyoxyethylene-hydrogenated | 0.05 |

-continued

| Composition: | |
|---|---|
| castor oil (50 E.O.) | |
| Methyl para-hydroxybenzoate | 0.1 |
| Perfume | 0.1 |
| Purified water | Balance to 100 |

Preparation Procedure

The high molecular sodium hyaluronate was dispersed in the purified water, followed by addition of the remaining ingredients. The resultant mixture was stirred thoroughly into the toilet water.

EXAMPLE 11

A milky lotion of the following composition was prepared:

| Composition: | |
|---|---|
| Stearic acid | 2.0 wt. % |
| Mineral oil | 6.0 |
| Squalane | 2.0 |
| Sorbitan monostearate | 1.5 |
| Polyoxyethylene sorbitan monostearate (20 E.O.) | 2.0 |
| Butyl para-hydroxybenzoate | 0.05 |
| High molecular sodium hyaluronate (molecular weight: 2,160,000; obtained in Example 2) | 0.2 |
| 1,3-Butylene glycol | 3.0 |
| Methyl para-hydroxybenzoate | 0.1 |
| Perfume | 0.15 |
| Purified water | Balance to 100 |

Preparation Procedure

The 1,3-butylene glycol and methyl para-hydroxybenzoate were added to the purified water, followed by dispersion of the high molecular sodium hyaluronate to obtain a dispersion. At 80° C., the dispersion was added to the mixture of the remaining ingredients other than the perfume, followed by emulsification. THe perfume was therafter added to the emulsion and the resultant mixture was then allowed to cool down to room temperature, thereby obtaining the milky lotion.

EXAMPLE 12

A cream of the following composition was prepared.

| Composition: | |
|---|---|
| Mineral oil | 23.0 wt. % |
| Petrolatum | 7.0 |
| Cetanol | 1.0 |
| Stearic acid | 2.0 |
| Bees wax | 2.0 |
| Sorbitan monostearate | 3.5 |
| Polyoxyethylene sorbitan monostearate (20 E.O.) | 2.5 |
| Butyl para-hydroxybenzoate | 0.05 |
| High molecular sodium hyaluronate (molecular weight: 2,160,000; obtained in Example 2) | 0.2 |
| 1,3-Butylene glycol | 3.0 |
| Methyl para-Hydroxybenzoate | 0.1 |
| Perfume | 0.15 |
| Purified water | Balance to 100 |

Preparation Procedure

The 1,3-butylene glycol and methyl para-hydroxybenzoate were added to the purified water, followed by dispersion of the high molecular sodium hyaluronate to obtain a dispersion. At 80° C., the dispersion was added to the mixture of the remaining ingredients other than the perfume, followed by emulsification. The perfume was thereafter added to the emulsion and the resultant mixture was then allowed to cool down to room temperature, thereby obtaining the cream.

EXAMPLE 13

A hair growth stimulant of the following composition was prepared.

| Composition: | |
|---|---|
| Ethanol | 40.0 wt. % |
| Perfume | 0.5 |
| Polyoxyethylene-hydrogenated castor oil (60 E.O.) | 1.0 |
| dl-α-Tocopherol acetate | 0.2 |
| Hinokitiol | 0.01 |
| Ethynyl estradiol | 0.0004 |
| Vitamin $B_6$.HCl | 0.2 |
| Pantothenyl ethyl ether | 0.5 |
| High molecular sodium hyaluronate (molecular weight: 2,160,000) | 0.1 |
| Purified water | Balance to 100 |

EXAMPLE 14

A hair rinse of the following composition was prepared.

| Composition: | |
|---|---|
| Stearyltrimethylammonium chloride | 4.5 wt. % |
| Stearic acid | 0.5 |
| Cetanol | 1.0 |
| Ethyleneglycol monostearate | 1.0 |
| Polyoxyethylene oleyl ether (2 E.O.) | 3.5 |
| 1,3-Butylene glycol | 3.0 |
| Perfume | 0.1 |
| High molecular sodium hyaluronate (molecular weight: 2,160,000) | 0.2 |
| Purified water | Balance to 100 |

EXAMPLE 15

A shampoo of the following composition was prepared.

| Composition: | |
|---|---|
| Sodium polyoxyethylene lauryl ether sulfate (3 E.O.) | 26.0 wt. % |
| Coconut fatty acid diethanol amide | 2.0 |
| Stearic acid | 1.0 |
| Ethylene glycol distearate | 1.0 |
| Sodium benzoate | 0.2 |
| Perfume | 0.1 |
| High molecular sodium hyaluronate (molecular weight: 2,160,000) | 0.2 |
| Purified water | Balance to 100 |

EXAMPLE 16

A foundation of the following composition was prepared.

| Ingredient | Amount |
|---|---|
| Stearic acid | 3.0 wt. % |
| Glyceryl monostearate self-emulsifying | 2.0 |
| Mineral oil | 5.0 |
| Amerchol L-101 (Amerchol Corporation) | 5.0 |
| 1,3-Butylene glycol | 5.0 |
| Triethanol amine | 0.5 |
| Methyl para-hydroxybenzoate | 0.2 |
| High molecular sodium hyaluronate (molecular weight: 2,160,000) | 0.2 |
| Kaolin | 8.49 |
| Titanium oxide | 7.0 |
| Red iron oxide | 0.5 |
| Yellow iron oxide | 1.0 |
| Black iron oxide | 0.001 |
| Perfume | 0.1 |
| Purified water | Balance to 100 |

EXAMPLE 17

Toilet waters of the compositions given in Table 6 were prepared. The feeling of their application was evaluated. Numerical values in Table 6 are by wt.%.

TABLE 6

| Ingredient | Invention Product 11 | Invention Product 12 | Comparative Product 9 | Comparative Product 10 |
|---|---|---|---|---|
| Sodium hyaluronate (m.w. 2,160,000) | 0.1 | 0.2 | — | 0.2 |
| Culture broth of lactic acid bacterium | 89.63 | 89.53 | 89.73 | — |
| Ethanol | 8.0 | 8.0 | 8.0 | 8.0 |
| 1,3-Butylene glycol | 2.0 | 2.0 | 2.0 | 2.0 |
| Methyl para-hydroxybenzoate | 0.12 | 0.12 | 0.12 | 0.12 |
| Perfume | 0.15 | 0.15 | 0.15 | 0.15 |
| Purified water | — | — | — | 89.53 |

Evaluation Method and Results

Each of the toilet waters of Table 6 was applied in a predetermined amount to the backs of the hands of 10 panellers (5 male panellers and 5 female panellers). It was evaluated by having each paneller fill out a questionnaire with respect to its spreadability on the skin, frictional feeling, stickiness, high-quality feeling, smoothness and moisturizing effects.

As a result, Invention Product 11 was found to show better feeling of application in each of the characteristics than Comparative Product 9. Invention Product 12 exhibited superior feeling of application to Comparative Product 10. Statistically significant differences were recognized between the feeling of application of the Invention Products and that of the Comparative Products, especially, in high-quality feeling and smoothness.

EXAMPLE 18

Milky lotions of the compositions given in Table 7 were prepared. The feeling of their application was evaluated. Numerical values in Table 7 are by wt.%.

TABLE 7

| Ingredient | Invention Product 13 | Comparative Product 11 | Comparative Product 12 |
|---|---|---|---|
| Sodium hyaluronate (m.w. 2,160,000) | 0.1 | 0.1 | — |
| Culture broth of lactic acid bacterium | 79.4 | — | 79.5 |
| Stearic acid | 2.5 | 2.5 | 2.5 |
| Beef tallow | 1.5 | 1.5 | 1.5 |
| Mineral oil | 6.0 | 6.0 | 6.0 |
| Methyl para-hydroxybenzoate | 0.3 | 0.3 | 0.3 |
| Sorbitan monostearate | 1.5 | 1.5 | 1.5 |
| Polyoxyethylene sorbitan monooleate | 2.5 | 2.5 | 2.5 |

TABLE 7-continued

| Ingredient | Invention Product 13 | Comparative Product 11 | Comparative Product 12 |
|---|---|---|---|
| (20 E.O.) | | | |
| 1,3-Butylene glycol | 6.0 | 6.0 | 6.0 |
| Perfume | 0.2 | 0.2 | 0.2 |
| Purified water | — | 79.4 | — |

Evaluation Method and Results

As a result of an evaluation in the same manner as in Example 17, Invention Product 13 showed superior feeling of application to Comparative Products 11 and 12. Statistically significant differences were recognized between the feeling of application of Invention Product 13 and that of Comparative Products 11 and 12, especially, in high-quality feeling and moisturizing effect.

EXAMPLE 19

Creams of the compositions given in Table 8 were prepared. The feeling of their application was evaluated. Numerical values in Table 8 are by wt.%.

TABLE 8

| Ingredient | Invention Product 14 | Comparative Product 13 | Comparative Product 14 |
|---|---|---|---|
| Sodium hyaluronate (m.w. 2,160,000) | 0.2 | 0.2 | — |
| Culture broth of lactic acid bacterium | 48.3 | — | 48.5 |
| Mineral oil | 23.0 | 23.0 | 23.0 |
| Octyldodecyl myristate | 5.0 | 5.0 | 5.0 |
| Petrolatum | 6.0 | 6.0 | 6.0 |
| Bees wax | 5.0 | 5.0 | 5.0 |
| Stearic acid | 2.0 | 2.0 | 2.0 |
| Behenyl alcohol | 1.0 | 1.0 | 1.0 |
| Sorbitan monostearate | 3.0 | 3.0 | 3.0 |
| Polyoxyethylene sorbitan monooleate (20 E.O.) | 3.0 | 3.0 | 3.0 |
| 1,3-Butylene glycol | 3.0 | 3.0 | 3.0 |
| Methyl para-hydroxybenzoate | 0.3 | 0.3 | 0.3 |
| Perfume | 0.2 | 0.2 | 0.2 |
| Purified water | — | 48.3 | — |

Evaluation Method and Results

As a result of an evaluation in the same manner as in Example 17, Invention Product 14 showed superior feeling of application to Comparative Products 13 and 14. Statistically significant differences were recognized between the feeling of application of Invention Product 14 and that of Comparative Products and 14, especially, in moisturizing effects and high-quality feeling.

EXAMPLE 20

A toilet water of the following composition was prepared.

| Composition: | |
|---|---|
| Ethanol | 10.0 wt. % |
| 1,3-Butylene glycol | 2.0 |
| High molecular sodium hyaluronate (molecular weight: 2,160,000) | 0.2 |
| Polyoxyethylene-hydrogenated castor oil (50 E.O.) | 0.05 |
| Methyl para-hydroxybenzoate | 0.1 |
| Perfume | 0.1 |
| Culture broth of lactic acid bacterium | Balance to 100 |

Preparation Procedure

The sodium hyaluronate was dispersed in the culture broth of the lactic acid bacterium, followed by addition of the remaining ingredients. The resultant mixture was stirred thoroughly into the toilet water.

EXAMPLE 21

A milky lotion of the following composition was prepared:

| Composition: | |
| --- | --- |
| Stearic acid | 2.0 wt. % |
| Mineral oil | 6.0 |
| Squalane | 2.0 |
| Sorbitan monostearate | 1.5 |
| Polyoxyethylene sorbitan monostearate (20 E.O.) | 2.0 |
| Butyl para-hydroxybenzoate | 0.05 |
| High molecular sodium hyaluronate (molecular weight: 2,160,000) | 0.2 |
| 1,3-Butylene glycol | 3.0 |
| Methyl para-hydroxybenzoate | 0.1 |
| Perfume | 0.15 |
| Culture broth of lactic acid bacterium | Balance to 100 |

Preparation Procedure

The 1,3-butylene glycol and methyl para-hydroxybenzoate were added to the culture broth of the lactic acid bacterium, followed by dispersion of the sodium hyaluronate to obtain a dispersion. At 80° C., the dispersion was added to the mixture of the remaining ingredients other than the perfume, followed by emulsification. The perfume was thereafter added to the emulsion and the resultant mixture was then allowed to cool down to room temperature, thereby obtaining the milky lotion.

EXAMPLE 22

A cream of the following composition was prepared.

| Composition: | |
| --- | --- |
| Mineral oil | 23.0 wt. % |
| Petrolatum | 7.0 |
| Cetanol | 1.0 |
| Stearic acid | 2.0 |
| Bees wax | 2.0 |
| Sorbitan monostearate | 3.5 |
| Polyoxyethylene sorbitan monostearate (20 E.O.) | 2.5 |
| Butyl para-hydroxybenzoate | 0.05 |
| High molecular sodium hyaluronate (molecular weight: 2,160,000) | 0.2 |
| 1,3-Butylene glycol | 3.0 |
| Methyl para-hydroxybenzoate | 0.1 |
| Perfume | 0.15 |
| Culture broth of lactic acid bacterium | Balance to 100 |

Preparation Procedure

The 1,3-butylene glycol and methyl para-hydroxybenzoate were added to the culture broth of the lactic acid bacterium, followed by dispersion of the sodium hyaluronate to obtain a dispersion. At 80° C., the dispersion was added to the mixture of the remaining ingredients other than the perfume, followed by emulsification. The perfume was thereafter added to the emulsion and the resultant mixture was then allowed to cool down to room temperature, thereby obtaining the cream.

Having now fully described the invention, it will be apparent to one of ordinary skill in the art that many changes and modifications can be made thereto without departing from the spirit or scope of the invention as set forth herein.

We claim:

1. A process for the production of hyaluronic acid, which comprises the steps:
    culturing in a culture medium *Streptococcus zooepidemicus* YIT 2030 (FERM BP-1305), and
    collecting said hyaluronic acid.

2. The strain of *Streptococcus zooepidemicus* which is *Streptococcus zooepidemicus* YIT 2030 (FERM BP-1305).

* * * * *

UNITED STATES PATENT AND TRADEMARK OFFICE
CERTIFICATE OF CORRECTION

PATENT NO. : 5,023,175

DATED : June 11, 1991

INVENTOR(S) : Hideo Hosoya et al.

It is certified that error appears in the above-identified patent and that said Letters Patent is hereby corrected as shown below:

On the title page, item [30]:
The second Priority data is incorrect, should be,

--May 1, 1986 [JP] JAPAN ..................61-99447--.

Signed and Sealed this

Sixteenth Day of March, 1993

Attest:

STEPHEN G. KUNIN

Attesting Officer

Acting Commissioner of Patents and Trademarks